United States Patent [19]

Jauw et al.

[11] Patent Number: 5,436,009
[45] Date of Patent: Jul. 25, 1995

[54] SUSTAINED RELEASE SUPPOSITORIES AND A PROCESS FOR PREPARATION

[75] Inventors: Tjoe H. Jauw, Amsterdam; Hendrik W. Frijlink, Huizen; Frits Moolenaar, Stitswerd; Peter Meijlink, Oosthuizen, all of Netherlands

[73] Assignee: Dagra Pharma B.V., Diemen, Netherlands

[21] Appl. No.: 990,888

[22] Filed: Dec. 15, 1992

[30] Foreign Application Priority Data

Dec. 20, 1991 [NL] Netherlands ............... 9102142

[51] Int. Cl.$^6$ .............................................. A61M 31/00
[52] U.S. Cl. ..................................... 424/436; 424/422; 424/434; 514/966
[58] Field of Search ............... 424/436, 422, 434; 514/966

[56] References Cited

U.S. PATENT DOCUMENTS

| | | | |
|---|---|---|---|
| 2,538,127 | 1/1951 | Saunders et al. | 514/263 |
| 3,870,790 | 3/1975 | Lowey | 424/19 |
| 4,070,494 | 1/1978 | Hoffmeister et al. | 424/2 |
| 4,265,875 | 5/1981 | Byrne | 424/19 |
| 4,344,968 | 8/1982 | Aoda | 424/365 |
| 4,369,172 | 1/1983 | Schor | 424/19 |
| 4,405,597 | 9/1983 | Takagishi | 424/35 |
| 4,406,883 | 9/1983 | Byrne et al. | 514/125 |

FOREIGN PATENT DOCUMENTS

| | | |
|---|---|---|
| 0103995 | 3/1984 | European Pat. Off. |
| 0359402 | 3/1990 | European Pat. Off. |
| 0391852 | 10/1990 | European Pat. Off. |
| 0430414 | 6/1991 | European Pat. Off. |
| 2530563 | 1/1977 | Germany |

OTHER PUBLICATIONS

JP 1,163,118, Jun. 1989, Abstract.

*Primary Examiner*—D. Gabrielle Phelan
*Attorney, Agent, or Firm*—Beveridge, DeGrandi, Weilacher & Young

[57] ABSTRACT

A sustained release suppository comprising in a usual suppository base
  a) a water-soluble therapeutically active substance, the average particle size of which is smaller than 20 $\mu$m,
  b) a physiologically acceptable organic substance which is swellable in contact with water, and
  c) hydrophobic silicium dioxide.

The suppository base is usually a fat having a melting range of from 29° to 38° C. As ingredient b) cellulose derivatives such as hydroxypropylmethylcellulose may be used, in a quantity of from 5 to 40% by weight, preferably 9 to 15% by weight. Ingredient c) is preferably used in a quantity of from 3 to 6% by weight. Also a process for manufacturing the suppositories is described.

29 Claims, 1 Drawing Sheet

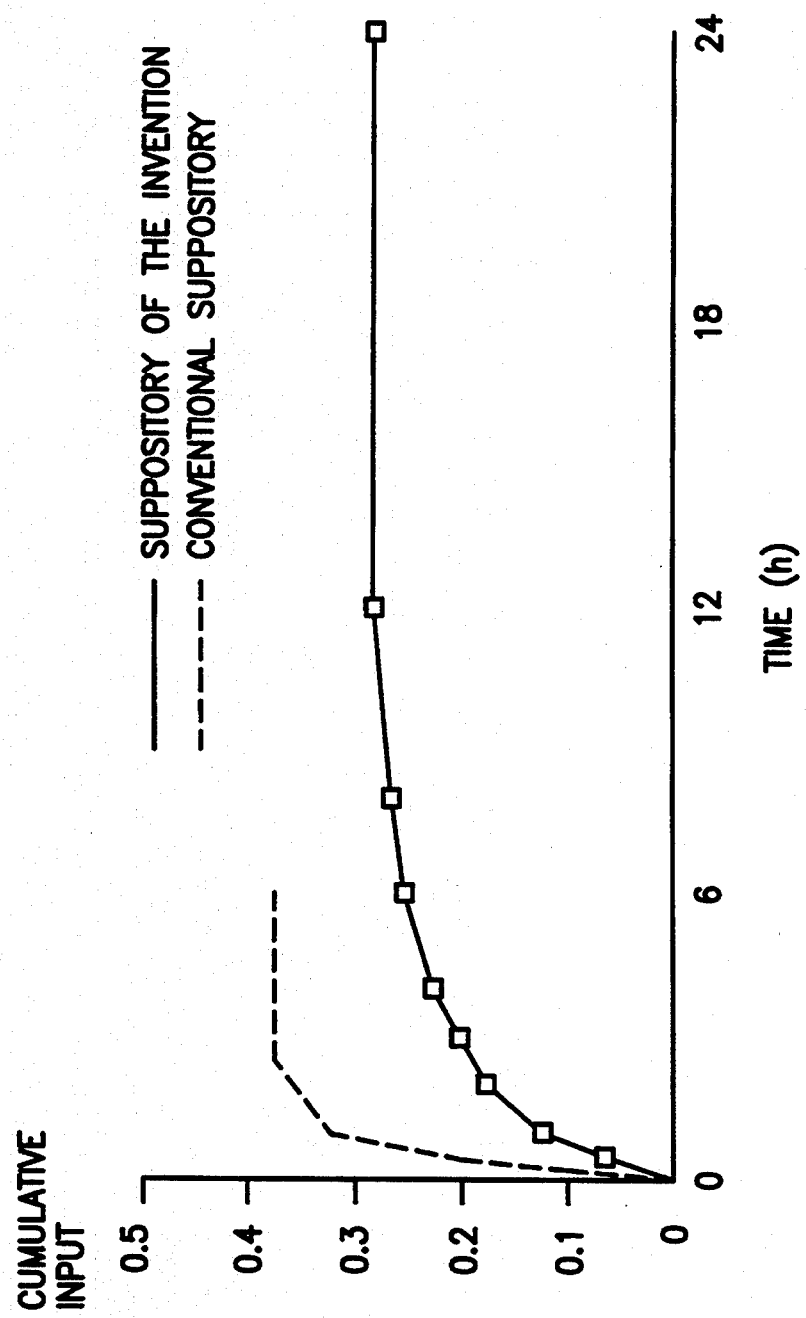

SUSTAINED RELEASE SUPPOSITORIES AND A PROCESS FOR PREPARATION

This invention relates to suppositories which slowly release the pharmacologically active substance. There are important reasons why it is often preferred to administer a drug rectally rather than orally: nausea, vomitting, stomach irritation, inability to swallow and the possibility to partly avoid the hepatic first pass clearance. A disadvantage of the rectal route is the lack of patient acceptability if a drug has to be administered frequently due to a short half time of the drug.

Conventional suppositories generally contain non-polar bases, such as Witepsol®, Estarinum®, Massupol®, etc. or polar bases, such as macrogols, various kinds of hydrophilic substances, gelatine, cellulose derivatives, in water. The release of a drug from these conventional suppositories is usually spontaneous.

It is known to use certain substances as a suppository base or to add substances to suppository bases in order to obtain sustained-release suppositories. Thus it is known to use organic polymers which swell in contact with water. These substances are being called concentration-viscosity increasing ingredients. U.S. Pat. Nos. 4,265,875 and 4,369,172 disclose suppository bases which mainly consist of hydroxypropylmethylcellulose. They show a sustained release of the active ingredients. Further it is known to use hydrophobic silicium dioxide (Aerosil®), a so-called fluid viscosity-increasing ingredient. Tukker et al., Acta Pharmaceutica Technologica 30 (2), 155–160, 1984, describe that adding colloidal hydrophobic silicium dioxide to Witepsol® suppository bases gives a sustained release of the active ingredient. Tabata et al, Yakuzaigaku, vol. 47, no. 3, 141–146 (1987), also describe the occurence of sustained release when adding some types of Aerosil®.

The application of the above-mentioned viscosity-increasing ingredients does, however, not guarantee a delayed drug release. In the case of the swellable polymers, sustained release does often not occur due to the rectal pressure which compresses the viscous hydrophilic mass against the rectum wall, and thus forming a viscous film, from where the active ingredient is readily absorbed. Only when very high concentrations are applied, a sustained release can be expected. But this cannot be realized technologically.

In the case of hydrophobic silicium dioxide, the delay of drug release is not taking place when a relatively low concentration of the substance is administered. In contrast, when a high concentration is used, the release of the active ingredient will be delayed substantially, but in this case the bioavailability is very low due to interfacial blocking (rectum-mucous/lipophilic viscous suppository mass).

The object of the present invention is to provide new suppositories which give a regular and sustained release of the active ingredient for a long period of time, and which give a good bioavailability of the active ingredient.

The invention provides a sustained release suppository comprising in a usual suppository base:
a) a water-soluble therapeutically active substance, the average particle size of which is smaller than 20 μm,
b) a physiologically acceptable organic substance which is swellable in contact with water, and
c) hydrophobic silicium dioxide.

BRIEF DESCRIPTION OF THE DRAWINGS

The present invention will be further understood with reference to the drawing, wherein FIG. 1 is a graph showing the average cumulative input (fraction of the absorbed dose of morphine in the plasma of thirteen volunteers) plotted against time for an example of the suppository of the present invention and for a conventional suppository.

The suppositories according to the invention show the following advantages compared to conventional suppositories:
the frequency of administration is limited to once or twice in 24 hours,
the peak concentration in the blood is lower and gives less fluctuation,
the safety increases, especially for drugs with a narrow therapeutical index, and
patient compliance is better.

As a suppository base, each fatty substance normally used for suppositories having a melting range of from 29° to 38° C. may be used, e.g. the hard fats which are used commonly. A suppository base consisting of a mixture of triglycerides of natural unsaturated vegetable fatty acids having 12 to 18 carbon atoms, to which are added partial glycerides of the same fatty acids in various quantities, is preferred.

Such a suppository base has for instance a melting range of from 33.5° to 37° C. Included are hard fats having a melting range of from 33.5° to 35.5° C. (rising melting point), an iodine colour number of up to 3, an iodine number of up to 3 and an unsaponifiable content of up to 0.3%. Particularly preferred are either hard fats having the above-mentioned properties, and additionally a softening point of 32.5° to 34.5° C., an acid number of up to 0.2, a saponification number of 230 to 240 and a hydroxyl number of up to 15, such as e.g. Witepsol® H15, or hard fats having additionally a softening point of 29.0° to 33.0° C., an acid number of up to 0.3, a saponification number of 225 to 240 and a hydroxyl number of 20 to 30, such as e.g. Witepsol® W25.

The quantity of the suppository base in the suppositories according to the invention is conveniently 55 to 90, in particular 66 to 87% by weight, based on the total mass of the suppository.

Almost all therapeutically active substances which are water-soluble and have an average particle size smaller than 20 μm, are suitable as therapeutically active substances for the suppositories according to the invention. Average particle size is used herein to mean that 80 to 100% of the active substance has a particle size below the indicated value (20 μm). Preferably, the particle size of the active substance is between 5 and 25, in particular between 10 and 20 μm. The concentration of active substance in the suppositories may be 0.1 to 7.5% by weight, based on the total mass of the suppository, and preferably 0.5 to 6% by weight, and most preferably 1 to 5% by weight.

Suitable active substances include e.g. water-soluble analgetics and physiologically acceptable salts thereof, in particular narcotic analgetics. Examples of such active substances include physiologically acceptable salts of morphine, such as morphine sulphate and morphine hydrochloride.

Ingredient b) in the suppositories according to the invention is a physiologically acceptable organic substance which is swellable in contact with water and increases the concentration-viscosity, both in the fatty suppository mass and in contact with rectum liquid. As ingredient b) e.g. non-ionic, for suppositories usual cellulose derivatives having a viscosity between 2500 and 7500 cp, preferably 3000 to 6000 cp, may be used (measurement of the viscosity in a 2% aqueous solution at 20° C.). Examples of suitable cellulose derivatives include hydroxypropylmethylcellulose, hydroxypropylcellulose, methylcellulose, hydroxyethylcellulose and (optionally cross-linked) carboxymethylcellulose. It is preferred to use hydroxypropylmethylcellulose (HPMC) having a viscosity of 3000 to 6000 cp, in particular an average viscosity of 4000 cp (HPMC 4000).

The quantity of ingredient b) in the suppositories according to the invention is in general 5 to 40% by weight, calculated on the total mass of the suppository, preferably 9 to 25% by weight and more preferably 9 to 15% by weight.

Ingredient c) in the suppositories according to the invention is hydrophobic silicium dioxide which is (pure) silicium dioxide that has obtained hydrophobic properties by chemically anchored methyl groups. Said product cannot be moistened with water. It is dispersable in all organic liquids and also in mixtures of water and water-mixable organic liquids. For a typical product, the following properties are given: $SiO_2+CH_3 > 99.8\%$, BET-surface area $110+20$ m$^2$/g, average particle size about 16 nm, carbon content 0.9 to 1.2%, which corresponds to about 0.6 to 0.8 mmol $CH_3/100$ m$^2$, loss of weight at 105° C. $<0.5\%$, loss of weight at 1000° C. $<2\%$, pH-value of a 4% suspension in methanol/water (1:1) 3.6 to 4.3, content of $HCl<0.05\%$, of $Al_2O_3<0.05\%$, of $TiO_2<0.03\%$ and of $Fe_2O_3<0.01\%$, tamping density about 50 g/l. Aerosil ® R972 is preferred.

The quantity of ingredient c) is suitably 0.5 to 7.5% by weight, calculated on the total mass of the suppository, and preferably 3 to 6% by weight. Ingredient b) is in general present in an excess amount over ingredient c). Preferably, the quantity of ingredient b) is the two- to fourfold of the quantity of ingredient c). However, it is also possible that the quantities of ingredients b) and c) are about the same.

It is especially preferred that the suppositories according to the invention have compositions within the following ranges:

| active substance | 30–150 mg |
|---|---|
| ingredient b) | 250–420 mg |
| ingredient c) | 80–108 mg |
| suppository base | 2390–2450 mg |

Preferably, the ingredients b) and c) have the same particle size or the same particle size distribution as the active substance a). In addition to the ingredients b) and c) the suppositories according to the invention may also contain other usual pharmaceutical adjuvants and additives.

The suppositories of the invention can be manufactured by any conventional method. For instance, the active substance, optionally after grinding it to an average particle size of less than 20 μm, can be mixed homogeneously in a manner known per se with the ingredients b) and c), and any usual adjuvants and additives, and subsequently the obtained mixture is either mixed with the melted suppository base at a temperature of 35° to 45° C. or is dispersed homogeneously in the melted suppository base.

The effect of the suppositories according to the invention has been shown in the following in vivo trial on thirteen volunteers. Seven male and six female healthy volunteers participated in the study. Before participation liver and kidney functions were determined and found normal. The morphine plasma concentration was measured by using the HPLC (High performance liquid chromatography) method with an electrochemical detector. This method was considered to be the most appropriate, since it determines only the pure morphine and is not disturbed by the occurence of metabolites (mainly morphine-3- and -6-glucuronides) in plasma, as is the case with a RIA (radio-immunoassay) method. The suppository used had the following composition:

| Morphine sulphate | 30 mg |
|---|---|
| HPMC 4000 | 300 mg |
| Aerosil ® R972 | 108 mg |
| Witepsol ® W25 | 2390 mg |

The result is shown in FIG. 1. In this Figure, the average cumulative input (fraction of the absorbed dose of morphine) is plotted against time. Further, for comparison, the average cumulative input is plotted after administration of a Witepsol ® suppository containing only 10 mg of morphine-HCl and 100 mg of lactose. The Figure clearly demonstrates that a sustained release of morphine from the suppository of the invention occurs. The invention is further illustrated by the following examples:

EXAMPLE I

Morphine sulphate suppositories: 30 mg per suppository; batch size: 270 suppositories = 756 g

| Morphine sulphate | 8.100 g |
|---|---|
| HPMC 4000 | 81.000 g |
| Aerosil ® R972 | 29.160 g |
| Witepsol ® W25 | 637.740 g |

Preparation

The morphine sulphate, HPMC 4000 and Aerosil ® R972 were sieved through 600 μm. The sieved powders were premixed in a cube mixer for 10 minutes. Witepsol ® W25 was melted on a water bath in a suitable bowl (maximum 50° C.). The premixed powder was added to the melted fat and mixed with a small Ultra Turrax until homogeneous. The fatty suspension was poured into a suppository filling machine and gently mixed until a temperature of about 34° C. was reached. Then the mixture was poured into plastic moulds of 3 ml. All suppositories were kept at room temperature for at least 24 hours.

EXAMPLE II

Morphine sulphate suppositories: 30 mg per suppository; batch size: 50000 suppositories = 140 kg

| Morphine sulphate | 1500 g |
|---|---|
| HPMC 4000 | 15000 g |
| Aerosil ® R972 | 5400 g |
| Witepsol ® W25 | 118100 g |

Preparation

The morphine sulphate, HPMC 4000 and Aerosil ® R972 were sieved through 600 μm. The sieved powders were premixed in a tumble mixer for 10 minutes. Witepsol® W25 was melted in a steam heated vessel equipped with a colloid mill. The premixed powders were added to the melted fat and mixed until homogeneous. The fatty suspension was transported through pre-heated pipes to a suppository filling line where the suppository moulds of 3 ml were filled. The suppositories were not exposed to shock-cooling and kept at room temperature for at least 24 hours.

We claim:

1. A solid, sustained release rectal suppository, said suppository comprising
   a) a water-soluble therapeutically active substance which is an analgetic or a physiologically acceptable salt thereof, the average particle size of which is smaller than 20 μm,
   b) a physiologically acceptable organic substance which is swellable in contact with water,
   c) hydrophobic silicon dioxide, wherein said hydrophobic silicon dioxide is pure silicon dioxide containing methyl groups, and
   d) a suppository base which is a fatty substance having a melting range of from 29° to 38° C.

2. The suppository according to claim 1, wherein said ingredient b) is present in at least the same quantity as said ingredient c) or in excess over said ingredient c).

3. The suppository according to claim 1, wherein said suppository contains 0.1 to 7.5% by weight of said active substance.

4. The suppository according to claim 1, wherein said active substance is a physiologically acceptable morphine salt.

5. The suppository according to claim 1, wherein said suppository contains 3 to 6% by weight of said ingredient c).

6. The suppository according to claim 1, wherein said suppository contains 5 to 40% by weight of said ingredient b).

7. The suppository according to claim 1, wherein said ingredient b) is a cellulose derivative having a viscosity between 2500 and 7500 cp.

8. A process for manufacturing the suppository according to claim 1, said process comprising optionally grinding said active substance to an average particle size of less than 20 μm, mixing said active substance, having an average particle size of less than 20 μm, homogeneously with ingredients b) and c), and adjuvants and additives to obtain a mixture, and subsequently mixing said mixture with a melted suppository base at a temperature of 35° to 45° C. or dispersing said mixture homogeneously in a melted suppository base.

9. The suppository according to claim 1, wherein said suppository base is 55 to 90% by weight of the total mass of said suppository.

10. The suppository according to claim 9, wherein said suppository base is 66 to 87% by weight of the total mass of said suppository.

11. The suppository according to claim 3, wherein said suppository contains 0.5 to 6% by weight of said active substance.

12. The suppository according to claim 11, wherein said suppository contains 1 to 5% by weight of said active substance.

13. The suppository according to claim 6, wherein said suppository contains 9 to 25% by weight of said ingredient b).

14. The suppository according to claim 13, wherein said suppository contains 9 to 15% by weight of said ingredient b).

15. The suppository according to claim 7, wherein said ingredient b) is a cellulose derivative having a viscosity between 3000 and 6000 cp.

16. The suppository according to claim 7, wherein said cellulose derivative is selected from the group consisting of hydroxypropylmethylcellulose, hydroxypropylcellulose, methylcellulose, hydroxyethylcellulose, carboxymethylcellulose, and cross-linked carboxymethylcellulose.

17. The suppository according to claim 16, wherein said ingredient b) is hydroxypropylmethylcellulose having a viscosity of 3000 to 6000 cp.

18. The suppository according to claim 17, wherein said ingredient b) is hydroxypropylmethylcellulose having an average viscosity of 4000 cp.

19. The suppository according to claim 1, wherein said suppository contains 0.5 to 7.5% by weight of said ingredient c).

20. The suppository according to claim 1, wherein the ratio of said ingredient b): said ingredient c) is 2 to 4:1.

21. The suppository according to claim 1, wherein said ingredient c) has the following properties: $SiO_2+CH_3>99.8\%$, BET-surface area $110\pm20$ m$^2$/g, average particle size about 16 nm, carbon content 0.9 to 1.2% or 0.6 to 0.8 mmol $CH_3/100$ m$^2$, loss of weight at 105° C.<0.5%, loss of weight at 1000° C.<2%, pH-value of 3.6 to 4.3 of a 4% suspension in methanol/water at a 1:1 ratio, content of HCl<0.05%, content of $Al_2O_3$<0.05%, content of $TiO_2$<0.03%, content of $Fe_2O_3$<0.01% and tamping density about 50 g/l.

22. The suppository according to claim 1, said suppository comprising 30 to 150 mg of said active substance, 250 to 420 mg of said ingredient b), 80 to 108 mg of said ingredient c), and 2390 to 2450 mg of said suppository base.

23. The suppository according to claim 1, said suppository base having a melting range of 33.5° to 37° C.

24. The suppository according to claim 1, said suppository base is a hard fat having a melting range of 33.5° to 35.5° C., an iodine color number of up to 3, an iodine number of up to 3, and an unsaponifiable content of up to 0.3%.

25. The suppository according to claim 24, said hard fat has a softening point of 32.5° to 34.5° C., an acid number of up to 0.2, a saponification number of 230 to 240, and a hydroxyl number of up to 15.

26. The suppository according to claim 24, said hard fat has a softening point of 29.0° to 33.0° C., an acid number of up to 0.3, and a saponification number of 225 to 230 and a hydroxyl number of 20 to 30.

27. The suppository according to claim 1, wherein said suppository base is a mixture of triglycerides of natural unsaturated vegetable fatty acids having 12 to 18 carbon atoms to which are added partial glycerides of said natural unsaturated vegetable fatty acids.

28. A solid sustained release rectal suppository, said rectal suppository consisting essentially of
   a) a water-soluble therapeutically active substance, the average particle size of which is smaller than 20 μm, wherein said water-soluble therapeutically active substance is an analgetic or a physiologically acceptable salt thereof,
   b) a physiologically acceptable organic substance which is swellable in contact with water, c) hydrophobic silicon dioxide, wherein said hydrophobic silicon dioxide is pure silicon dioxide containing methyl groups, and d) a suppository base which is a fatty substance having a melting range of from 29° to 38° C.

29. A process for using a sustained release suppository, said process comprising rectally administering to a patient in need thereof a sustained release suppository comprising a) a water-soluble therapeutically active substance, the average particle size of which is smaller than 20 μm, b) a physiologically acceptable organic substance which is swellable in contact with water, c) hydrophobic silicon dioxide, and d) a suppository base which is a fatty substance having a melting range of from 29° to 38° C.

* * * * *